US010314479B2

(12) United States Patent
Angeley et al.

(10) Patent No.: US 10,314,479 B2
(45) Date of Patent: *Jun. 11, 2019

(54) LASER EYE SURGERY SYSTEM

(71) Applicant: OPTIMEDICA CORPORATION, Santa Ana, CA (US)

(72) Inventors: David Angeley, Charlotteville, VA (US); Zhao Wang, San Carlos, CA (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 226 days.

This patent is subject to a terminal disclaimer.

(21) Appl. No.: 15/245,097

(22) Filed: Aug. 23, 2016

(65) Prior Publication Data

US 2016/0360960 A1 Dec. 15, 2016

Related U.S. Application Data

(63) Continuation of application No. 14/069,042, filed on Oct. 31, 2013, now Pat. No. 9,445,946.

(60) Provisional application No. 61/722,048, filed on Nov. 2, 2012.

(51) Int. Cl.
*A61B 3/10* (2006.01)
*A61F 9/008* (2006.01)

(52) U.S. Cl.
CPC .......... *A61B 3/102* (2013.01); *A61F 9/00825* (2013.01); *A61F 2009/0087* (2013.01); *A61F 2009/00846* (2013.01); *A61F 2009/00851* (2013.01); *A61F 2009/00872* (2013.01); *A61F 2009/00889* (2013.01)

(58) Field of Classification Search
CPC .................. A61B 5/0066; A61B 3/102; A61B 2090/3735; G01B 9/02091; A61F 2009/00851

See application file for complete search history.

(56) References Cited

U.S. PATENT DOCUMENTS

| 4,585,345 | A | * | 4/1986 | Inoue .................... G01J 3/4537 356/455 |
|---|---|---|---|---|
| 5,071,251 | A | | 12/1991 | Hochberg et al. |
| 5,383,199 | A | | 1/1995 | Laudenslager et al. |
| 5,459,570 | A | | 10/1995 | Swanson et al. |
| 5,720,894 | A | | 2/1998 | Neev et al. |

(Continued)

*Primary Examiner* — Niketa I Patel
*Assistant Examiner* — Nathan A Baldwin
(74) *Attorney, Agent, or Firm* — Johnson & Johnson Surgical Vision, Inc.

(57) ABSTRACT

A laser eye surgery system includes a laser source, a ranging subsystem, an integrated optical subsystem, and a patient interface assembly. The laser source produces a treatment beam that includes a plurality of laser pulses. The ranging subsystem produces a source beam used to locate one or more structures of an eye. The ranging subsystem includes an optical coherence tomography (OCT) pickoff assembly that includes a first optical wedge and a second optical wedge separated from the first optical wedge. The OCT pickoff assembly is configured to divide an OCT source beam into a sample beam and a reference beam. The integrated optical subsystem is used to scan the treatment beam and the sample beam. The patient interface assembly couples the eye with the integrated optical subsystem so as to constrain the eye relative to the integrated optical subsystem.

22 Claims, 8 Drawing Sheets

(56) References Cited

U.S. PATENT DOCUMENTS

| | | | |
|---|---|---|---|
| 5,748,352 | A | 5/1998 | Hattori |
| 5,748,898 | A | 5/1998 | Ueda |
| 5,847,828 | A | 12/1998 | Downs |
| 5,957,915 | A | 9/1999 | Trost |
| 5,984,916 | A | 11/1999 | Lai |
| 6,019,472 | A | 2/2000 | Koester et al. |
| 6,053,613 | A | 4/2000 | Wei et al. |
| 6,111,645 | A | 8/2000 | Tearney et al. |
| 6,454,761 | B1 | 9/2002 | Freedman |
| 7,289,222 | B1 | 10/2007 | Schuster |
| 7,352,512 | B2 | 4/2008 | Seiden et al. |
| 7,633,624 | B1 | 12/2009 | Wickholm |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 2007/0093795 | A1 | 4/2007 | Melcher et al. |
| 2010/0097682 | A1* | 4/2010 | Angeley ............. A61F 9/00821 359/227 |
| 2011/0019285 | A1* | 1/2011 | Kuo ................... G02B 27/0025 359/637 |
| 2011/0202046 | A1* | 8/2011 | Angeley ................ G06T 7/149 606/6 |
| 2011/0255088 | A1 | 10/2011 | Dane et al. |
| 2011/0319873 | A1 | 12/2011 | Raksi et al. |
| 2011/0319875 | A1 | 12/2011 | Loesel et al. |

\* cited by examiner

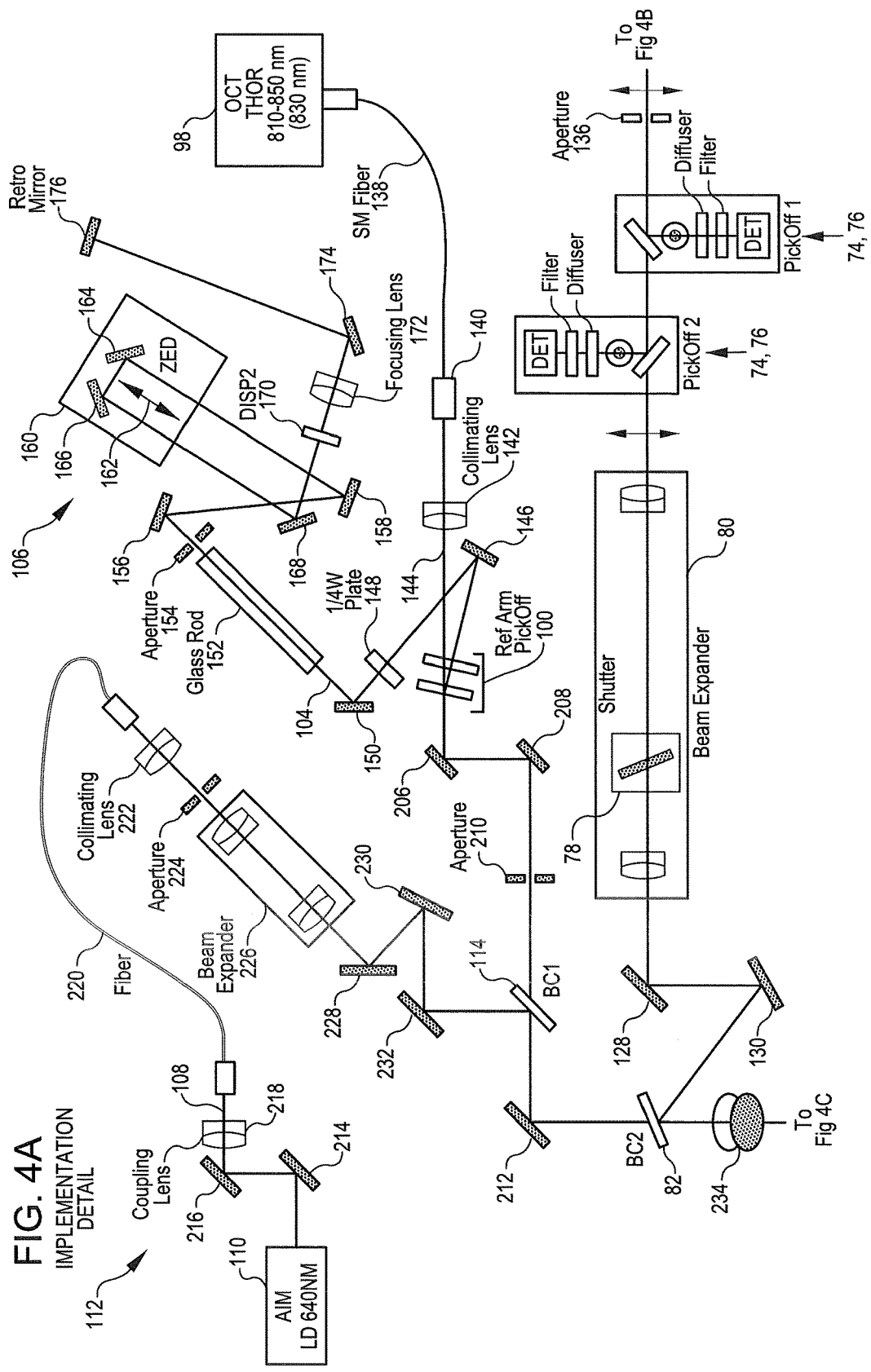

IMPLEMENTATION
DETAIL (cont')

IMPLEMENTATION DETAIL (cont')

LASER EYE SURGERY SYSTEM

CROSS REFERENCE TO RELATED APPLICATIONS

This application is a continuation of and claims priority to U.S. patent application Ser. No. 14/069,042, filed Oct. 31, 2013, which claims the benefit of priority to U.S. Provisional Application No. 61/722,048, filed Nov. 2, 2012, the entire contents of which are hereby incorporated by reference in their entirety for all purposes as if fully set forth herein.

BACKGROUND

Cataract extraction is one of the most commonly performed surgical procedures in the world. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy provides access for the next step of nuclear sculpting by phacoemulsification. Due to a variety of complications associated with the initial can-opener technique, attempts were made by leading experts in the field to develop a better technique for removal of the circular fragment of the anterior lens capsule prior to the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior lens capsule provides access for tool insertion during removal of the nucleus and for IOL insertion, a permanent aperture for transmission of the image to the retina of the patient, and also support of the IOL inside the remaining lens capsule that limits the potential for dislocation. The resulting reliance on the shape, symmetry, uniformity, and strength of the remaining lens capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the lens capsule due to lack of red reflex, to grasp the lens capsule with sufficient security, and to tear a smooth circular opening in the lens capsule of the appropriate size and in the correct location without creating radial rips and extensions. Also present are technical difficulties related to maintenance of the depth of the anterior chamber depth after opening the lens capsule, small pupils, or the absence of a red reflex due to the lens opacity. Some of the problems with visualization can be minimized through the use of dyes such as methylene blue or indocyanine green. Additional complications may also arise in patients with weak zonules (typically older patients) and very young children that have very soft and elastic lens capsules, which are very difficult to controllably and reliably rupture and tear.

The implantation of a "Bag-in-Lens" IOL typically uses anterior and posterior openings in the lens capsule of the same size. Manually creating matching anterior and posterior capsulotomies for the "Bag-in-Lens" configuration, however, is particularly difficult.

Many cataract patients have astigmatic visual errors. Astigmatism can occur when the corneal curvature is unequal in all directions. An IOL can be used to correct for astigmatism but requires precise rotational and central placement. Additionally, IOLs are not typically used for correction beyond 5 D of astigmatism. Many patients, however, have astigmatic visual errors exceeding 5 D. Higher correction beyond 5 D typically requires reshaping the cornea to make it more spherical. There are numerous existing approaches for reshaping the cornea, including Corneaplasty, Astigmatic Keratotomy, Corneal Relaxing Incision (CRI), and Limbal Relaxing Incision (LRI). In Astigmatic Keratotomy, Corneal Relaxing Incision (CRI), and Limbal Relaxing Incision (LRI), corneal incisions are made in a well-defined manner and depth to allow the cornea to change shape to become more spherical. Presently, these corneal incisions are typically accomplished manually often with limited precision.

Thus, improved methods and systems for treating cataracts and/or creating corneal incisions are needed.

SUMMARY

Improved laser eye surgery systems, and related methods, are provided. The laser eye surgery systems use a laser to form precise incisions in the cornea, in the lens capsule, and/or in the crystalline lens nucleus. In many embodiments, a laser eye surgery system includes a laser cutting subsystem to produce a laser pulse treatment beam to incise tissue within the eye, a ranging subsystem to measure the spatial disposition of external and internal structures of the eye in which incisions can be formed, an alignment subsystem, and shared optics operable to scan the treatment beam, a ranging subsystem beam, and/or an alignment beam relative to the laser eye surgery system. The alignment subsystem can include a video subsystem that can be used to, for example, provide images of the eye during docking of the eye to the laser eye surgery system. In many embodiments, a liquid interface is used between a patient interface lens and the eye. The use of the liquid interface avoids imparting undesirable forces to the patient's eye. The alignment and ranging subsystems may be used to detect structures involved with the patient interface.

Thus, in one aspect, a laser eye surgery system is provided. The laser eye surgery system includes a laser source, a ranging subsystem, an integrated optical subsystem, and a patient interface assembly. The laser source is configured to produce a treatment beam that includes a plurality of laser pulses. The ranging subsystem is configured to produce a source beam used to locate one or more structures of an eye. The ranging subsystem includes an optical coherence tomography (OCT) pickoff assembly that includes a first optical wedge and a second optical wedge separated from the first optical wedge. The OCT pickoff assembly is configured to divide the source beam into a sample beam and a reference beam. The integrated optical subsystem is configured to receive the treatment beam, direct the treatment beam to selected treatment locations within the eye so as to incise tissue at the selected treatment locations, receive the sample beam, direct the sample beam to selected measurement locations within the eye, and transmit return portions of the sample beam from the selected measurement locations back to the ranging subsystem for processing by the ranging subsystem. The patient interface assembly is configured to couple the eye with the integrated optical subsystem so as to constrain the eye relative to the integrated optical subsystem and provide coupling of treatment and ranging light to and within the eye.

Variations of the laser eye surgery system are provided. For example, the patient interface assembly can include a patient interface lens having a posterior surface spaced from the eye when the patient interface assembly couples the eye with the integrated optical subsystem. The patient interface assembly can be configured to accommodate a volume of fluid interfaced with both the patient interface lens posterior surface and the eye. The patient interface assembly can be configured to demountably couple with the integrated optical subsystem to enable replacement of the patient interface assembly between treatments. The patient interface assembly can be, for example, a removable assembly, an interchangeable assembly, and/or an exchangeable assembly. The patient interface lens can have an anterior surface disposed between the patient interface lens posterior surface and the integrated optical subsystem. The ranging subsystem can be used to locate the patient interface lens anterior surface and the patient interface lens posterior surface relative to the ranging subsystem and the integrated optical subsystem. The integrated optical subsystem can be controlled in part based on the locations of the patient interface lens anterior and posterior surfaces so as to at least one of said direct the treatment beam to selected treatment locations within the eye to incise tissue at the selected treatment locations or said direct the sample beam to selected measurement locations within the eye. The OCT ranging subsystem is split into a reference and sample beam. This splitting may be achieved using two optical wedges. Each of the first and second optical wedges can have non-parallel anterior and posterior surfaces. The source beam can propagate through the first optical wedge and into the second optical wedge. The second optical wedge posterior surface can be partially reflective so as to divide the source beam into the sample beam and the reference beam. The sample beam can propagate out of the second optical wedge through the posterior surface. The reflected reference beam can propagate out of the second optical wedge through the anterior surface and propagate back through the first optical wedge and along a reference optical path. A returning portion of the sample beam can be at least one of retro-reflected or scattered and returned back through the second optical wedge. The sample beam returning portion can propagate back through the first optical wedge. The reference beam, after traversing a path length, can be retro-reflected and can propagate back into the second optical wedge through the anterior surface. A reflected portion of the reference beam can then be reflected by the second optical wedge posterior surface. The reference beam reflected portion can propagate out of the second optical wedge through the anterior surface and propagate through the first optical wedge. The first and second optical wedges can have the same wedge angle and be arranged such that the wedge angles are opposing. The wedge angle of the first and second optical wedges can be in a range from 3 degrees to 10 degrees. The wedge angle of the first and second optical wedges can be in a range from 5 degrees to 7 degrees. The first and second optical wedges can be made from the same material having a refractive index of greater than 1.50 with respect to the wavelength of the source beam. The refractive index can be greater than 1.70 with respect to the wavelength of the source beam. The first optical wedge anterior and posterior surfaces can have an anti-reflection coating. The second optical wedge anterior surface can have the anti-reflection coating. The second optical wedge posterior surface can be uncoated. The anti-reflection coating can be magnesium fluoride ($MgF_2$). The source beam can have an angle of incidence on the second optical wedge posterior surface of less than 25 degrees. The angle of incidence can be less than 15 degrees. The OCT pickoff assembly comprised of the two wedges, for example, can be configured to have low angles of incidence at all surfaces such that the OCT pickoff assembly is substantially polarization insensitive. The first and second optical wedges can be separated by a distance greater than a detection range of the ranging subsystem to inhibit etalon effects. The second optical wedge anterior surface and the first optical wedge posterior surface can be non-parallel to inhibit etalon effects. The second optical wedge anterior surface and the first optical wedge posterior surface can deviate from parallel by 0.25 degrees to 3.0 degrees to inhibit etalon effects. The second optical wedge anterior surface and the first optical wedge posterior surface can deviate from parallel by 0.50 degrees to 1.5 degrees to inhibit etalon effects.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 4A, 4B, and 4C are different views of a simplified diagram illustrating the configuration of an optical assembly of a laser eye surgery system, in accordance with many embodiments.

DETAILED DESCRIPTION

Methods and systems related to laser eye surgery are disclosed. A laser is used to form precise incisions in the cornea, in the lens capsule, and/or in the crystalline lens nucleus. In many embodiments, a laser eye surgery system includes a laser cutting subsystem to produce a laser pulse treatment beam to incise tissue within the eye, a ranging subsystem to measure the spatial disposition of external and internal structures of the eye in which incisions can be formed, an alignment subsystem, and shared optics operable to scan the treatment beam, a ranging subsystem beam, and/or an alignment beam relative to the laser eye surgery system. The alignment subsystem can include a video subsystem that can be used to, for example, provide images of the eye during docking of the eye to the laser eye surgery system and also provide images of the eye once the docking process is complete. In many embodiments, a liquid interface is used between a patient interface lens and the eye. The use of the liquid interface avoids imparting undesirable forces to the patient's eye.

System Configuration

Figure 1:
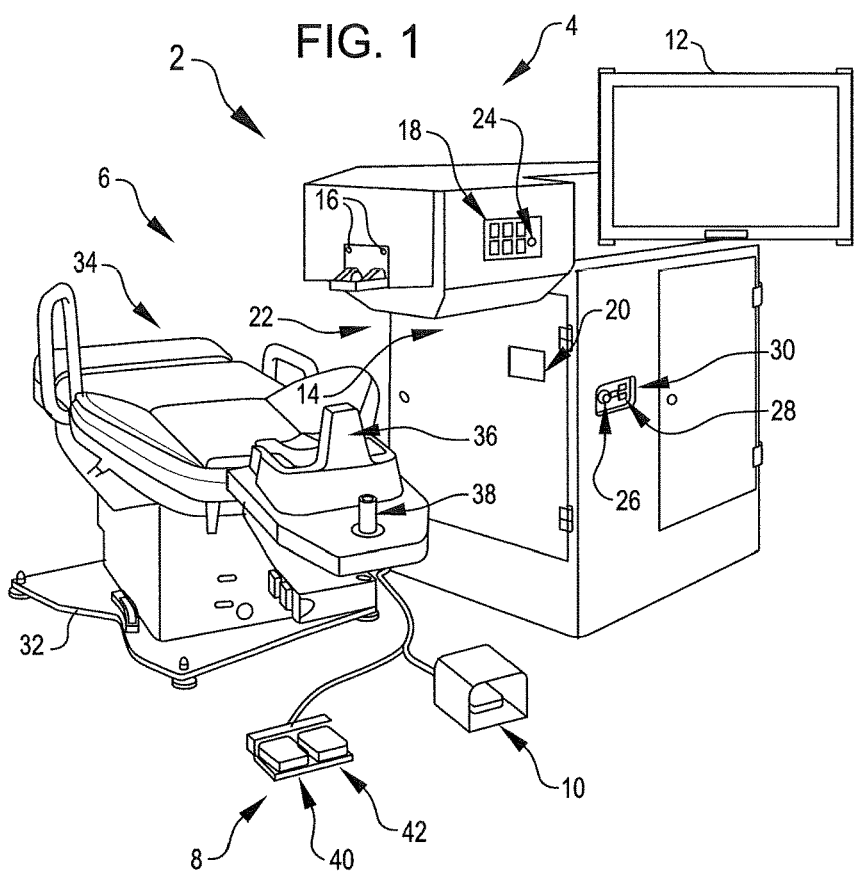
FIG. 1 is a perspective view showing a laser eye surgery system, in accordance with many embodiments.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
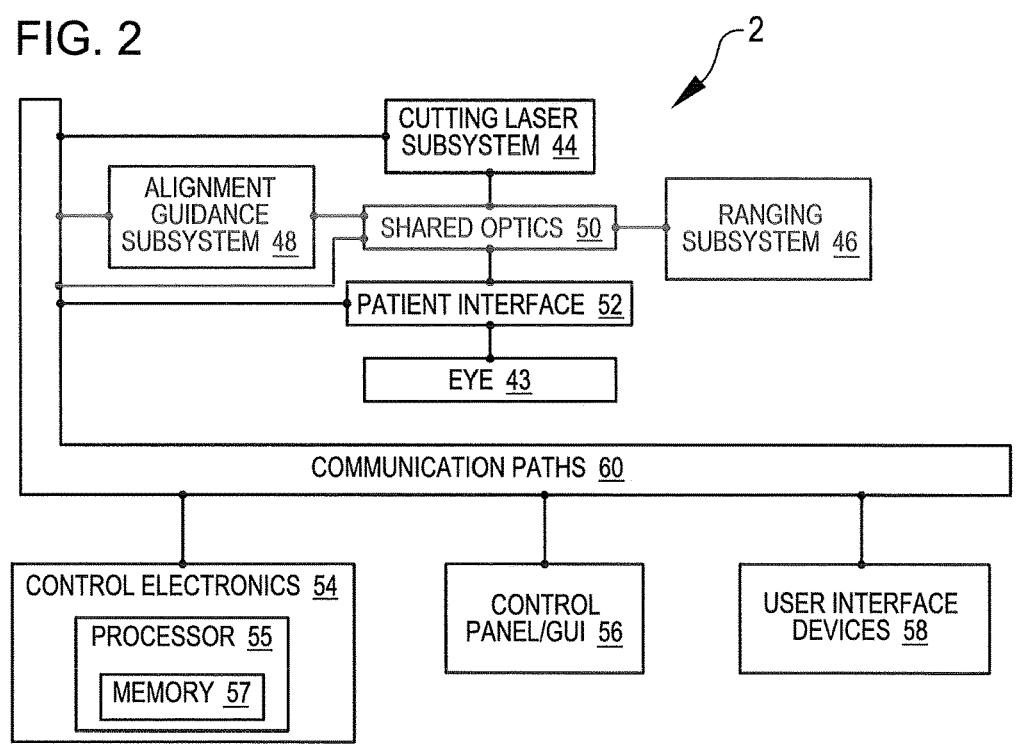
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
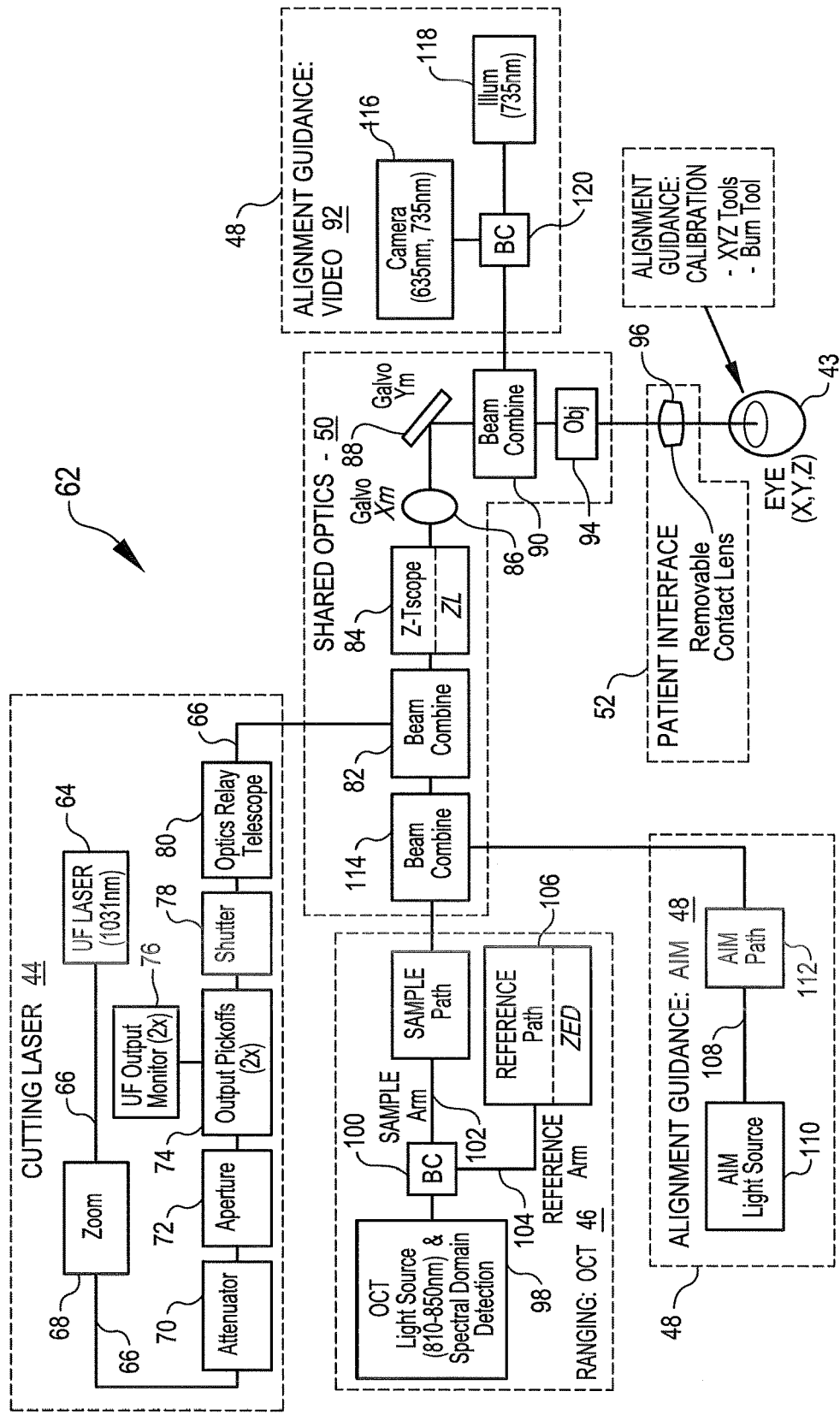
FIG. 3 is a simplified block diagram illustrating the configuration of an optical assembly of a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the XY galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a Z-scan device for scanning the focus point of the laser-pulse beam 66 in the patient's eye 43. The Z-telescope 84 can be controlled automatically and dynamically by the control electronics 54 and selected to be independent or to interplay with the X- and Y-scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-scan device 86 and the Y-scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source maybe be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be an suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 4B:
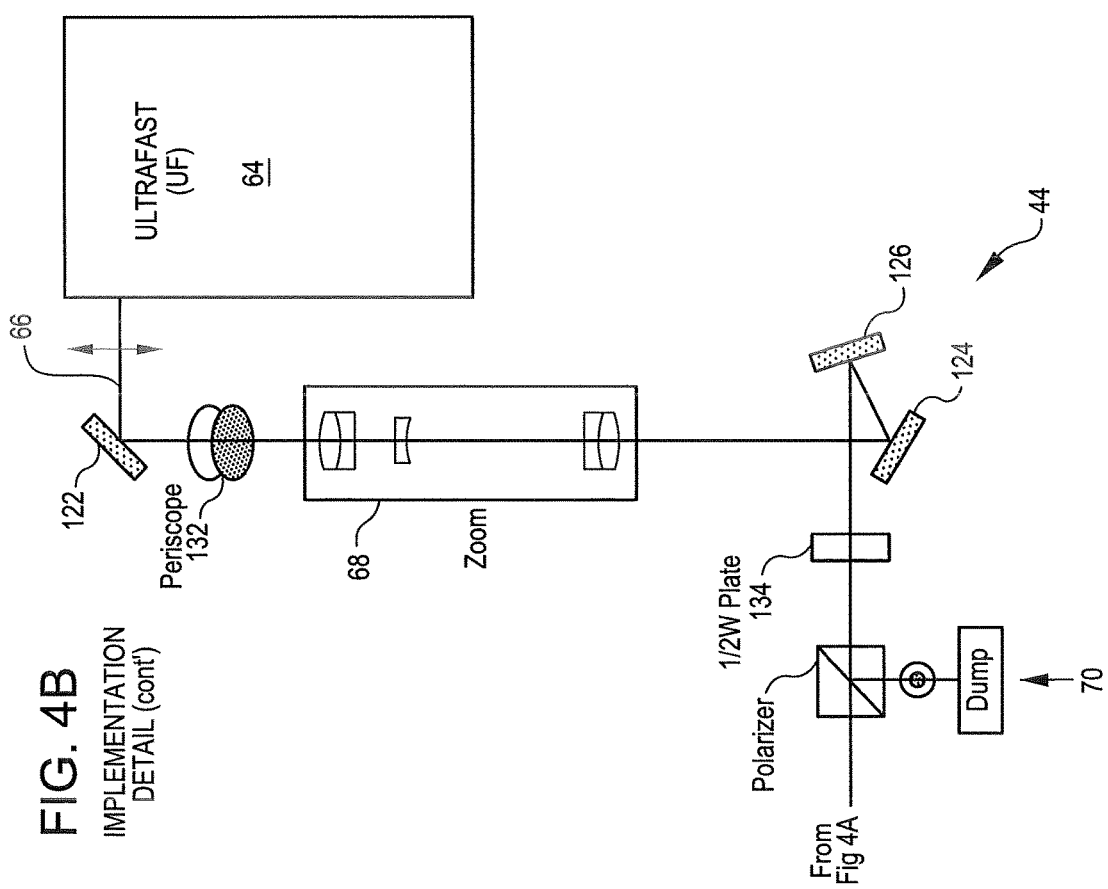
Figure 4C:
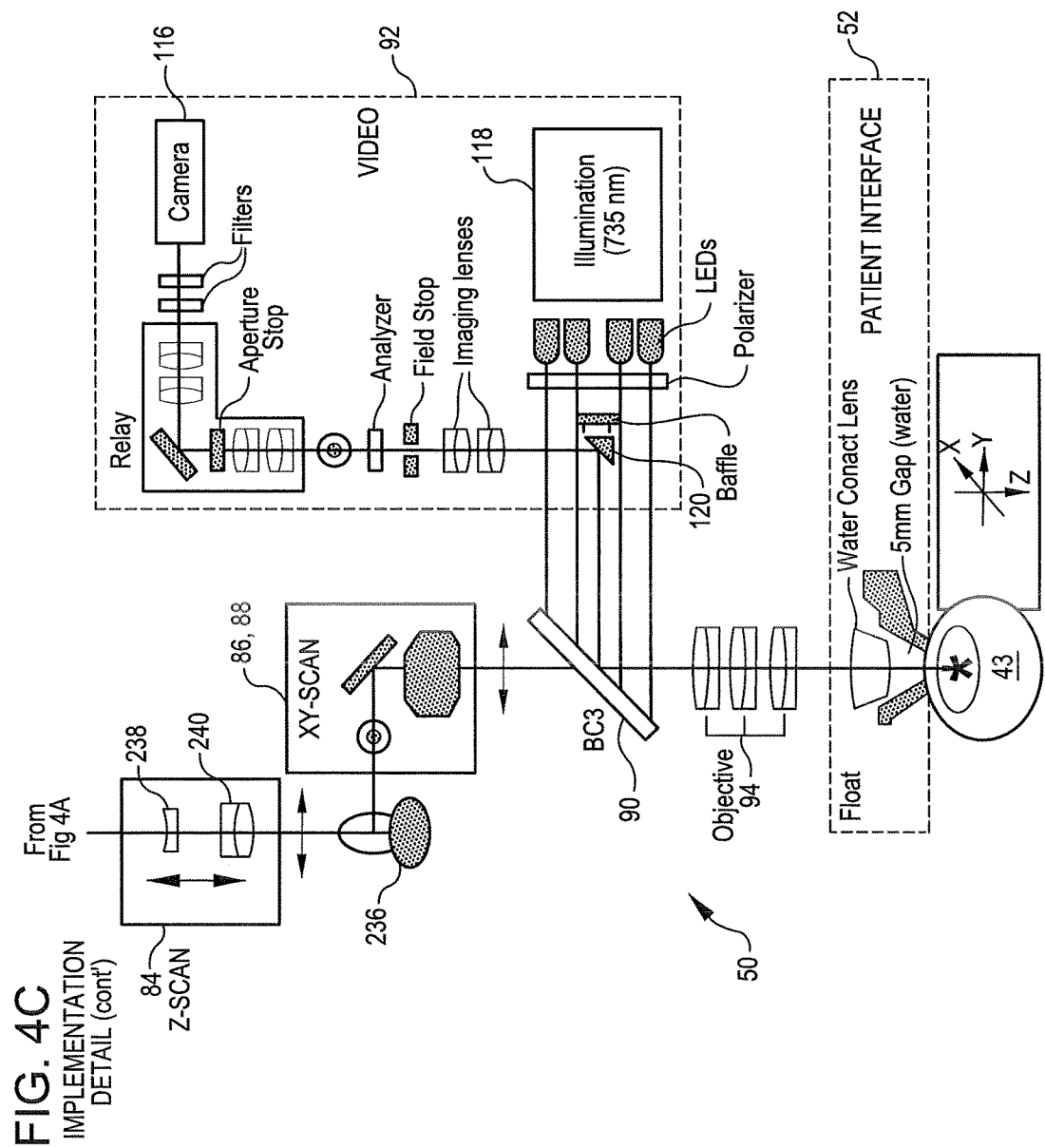

In the embodiment of FIGS. 4A, 4B, and 4C, the cutting laser subsystem 44 includes the ultrafast (UF) laser 64, the zoom assembly 68, the polarizer and beam dump 70, the output pickoffs 74, the output monitors 76, the system-controlled shutter 78, and the optics relay telescope 80. The cutting laser subsystem 44 further includes mirrors 122, 124, 126, 128, 130, a periscope 132, a one-half wave plate 134, and an aperture 136. The mirrors 122, 124, 126, 128, 130 are used to route the laser pulse beam 66 (treatment beam) from the ultrafast (UF) laser 64 to the beam combiner 82. The periscope 132 provides an adjustable means to align the laser pulse beam 66 output by the ultrafast (UF) laser 64 with the downstream optical path through the downstream portion of the cutting laser subsystem 44, the shared optics 50, the patient interface 52, and into the eye 43. The aperture 136 sets an outer useful diameter for the laser pulse beam 66.

The laser pulse beam 66 passes through the zoom assembly 68. The zoom assembly can be operable to modify beam parameters such as beam diameter, divergence, circularity, and astigmatism. For example, the zoom assembly 68 illustrated in FIG. 4B is adjustable and includes a three optical element assembly that is adjustable to achieve intended beam size and collimation. Although not illustrated here, an anomorphic or other optical system can be used to achieve desired beam parameters. The factors used to determine suitable beam parameters include the output beam parameters of the laser, the overall magnification of the system, and the desired numerical aperture (NA) at the treatment location. In addition, the zoom assembly 68 can be used to image a laser waist location or other preferred plane within the laser assembly 64 to the aperture 136 location, shown in FIG. 4A, for example. The aperture is then imaged by relay 80 to a center location between the X-scan device 86 and the Y-scan device 88, shown in FIG. 4C. In this way, the beam at the desired location in the laser such as a waist of stable location is placed at the aperture and the portion of the laser pulse beam 66 that makes it through the aperture 136 is assured to make it through the shared optics 50.

After exiting the zoom assembly 68, the laser pulse beam 66 is reflected by the mirror 124 and the mirror 126 and then passes through the one-half wave plate 134 before passing through the polarizer 70. The beam exiting the laser is linearly polarized. The ½ wave plate can rotate this polarization. The amount of light passing through the polarizer depends on the angle of the rotation of the linear polarization. Therefore the ½w plate with the polarizer acts as an attenuator of the beam that is transmitted through towards the shared optics. The rejected light from this attenuation method is directed into the beam dump. After exiting the one-half wave plate 134 and polarizer 70 combination, the laser pulse beam 66 passes through the aperture 136, through the output pickoffs 74, and through the optics relay telescope 80 and the system-controlled shutter 78. By locating the system-controlled shutter 78 downstream of the output pickoffs and monitors 74, 76, the power of the laser pulse beam 66 can be checked before opening the system-controlled shutter 78. After exiting the optics relay telescope 80, the laser pulse beam 66 is reflected by the mirror 128 and the mirror 130. The mirrors 122, 124, 126, 128, 130 in the cutting laser subsystem 44 can include a coating(s) to control dispersion so as to prevent broadening of the temporal pulse width. The beam combiner 82 then reflects the laser pulse beam 66 so as to be directed through the shared optics 50.

In the embodiment of FIGS. 4A, 4B, and 4C the ranging subsystem 46 includes the OCT light source and detection device 98, the pickoff/combiner assembly 100, and the reference path 106. The OCT light source and detection device 98 emits the OCT source beam 144, which propagates to the pickoff/combiner assembly 100 through a single mode optical fiber 138 and an optical fiber connector 140. The OCT source beam 144 is collimated using a lens 142 and proceeds towards the pickoff/combiner assembly 100. The function of the pickoff/combiner assembly 100 is to split the OCT source beam 144 into two separate beams (i.e., the sample beam 102 and the reference beam 104). The sample beam 102 propagates along an optical path referred to as a sample path. The reference beam 104 propagates along an optical path referred to as the reference path 106. As described herein, the sample beam 102 propagates to the eye 43 and is retro reflected or scattered back through the sample path to the pickoff/combiner assembly 100.

The reference beam 104 propagates away from and back to the pickoff/combiner assembly 100 along the reference path 106. The reference path 106 has an adjustable optical path length to extend the measurement range within the eye of the ranging subsystem 46. After leaving the pickoff/combiner assembly 100, the reference beam 104 is reflected by a mirror 146 so as to pass through an OCT quarter-wave plate 148. After exiting the OCT quarter-wave plate 148, the reference beam 104 is reflected by a mirror 150 so as to pass lengthwise through a glass rod 152. The material and the length of the glass rod 152 are selected to balance dispersion between the sample path and the reference path 106. After exiting the glass rod 152, the reference beam 104 passes through an aperture 154 and is then reflected by mirrors 156, 158 so as to be directed into a reference path length adjustment mechanism 160, which is repositionable along a direction 162. The mechanism 160 includes two mirrors 164 and 166, which are repositioned along the direction 162 by repositioning the mechanism 160 along the direction 162. The reference beam 104 entering the mechanism 160 is reflected by the mirrors 164, 166. After exiting the mechanism 160, the reference beam 104 is reflected by a mirror 168 so as to be directed through a dispersion element 170, which in combination with the glass rod 152 is selected to balance dispersion between the sample path and the reference path 106. After exiting the dispersion element 170, the reference beam 104 passes through a focusing lens 172 and is reflected by a mirror 174 toward a retro mirror 176. The retro mirror 176 retro-reflects the reference beam back along the reference path 106 to the pickoff/combiner assembly 100. The returning sample and reference beams are then combined by the pickoff/combiner assembly 100. The combined beams with embedded signal information is then directed back through the optical fiber 138 to the OCT light source and detection device 98 where the combined beams are detected.

Figure 5:
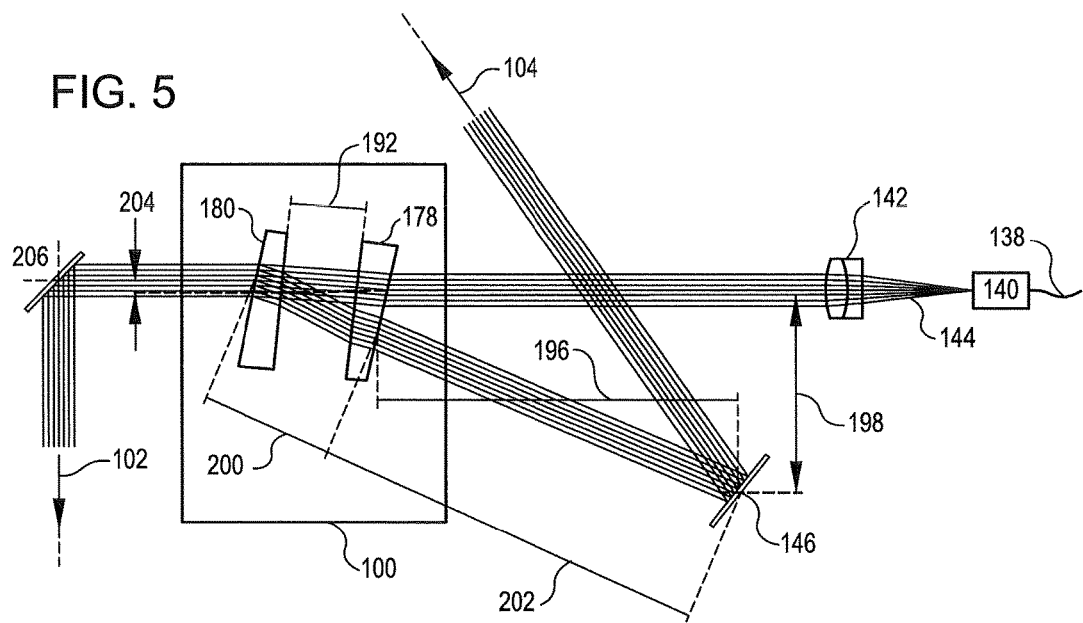
FIGS. 5 and 6 are simplified diagrams illustrating an OCT pickoff/combiner assembly, in accordance with many embodiments.
Figure 6:
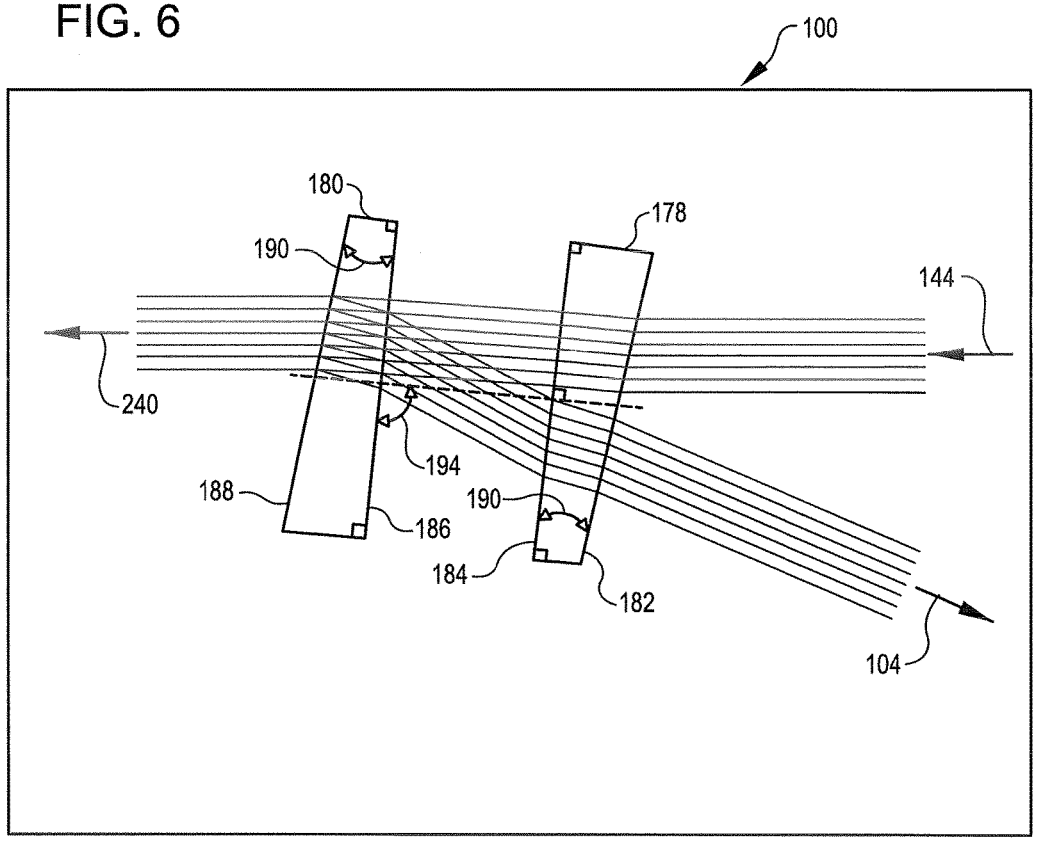

Referring now to FIGS. 5 and 6, the pickoff/combiner assembly 100 is described relative to dividing the OCT source beam 144 into the sample beam 102 and the reference beam 104. The division of the OCT source beam 144 is referred to herein as the pickoff mode. The pickoff/combiner assembly 100 also functions in what is referred to herein as the combiner mode in which the returning portion of the sample beam 102 and the returning reference beam 104 are combined and directed back to the OCT light source and detection device 98. The combiner mode works similar to the pickoff mode, but in reverse.

The pickoff/combiner assembly 100 includes a first optical wedge 178 and a second optical wedge 180. The OCT source beam 144 passes through the first optical wedge 178 and into the second optical wedge 180. The first optical wedge 178 has an anterior surface 182 and a posterior surface 184. The second optical wedge 180 has an anterior surface 186 and a posterior surface 188. The OCT source beam 144 enters the first optical wedge 178 through the anterior surface 182 and exits the first optical wedge 178 through the posterior surface 184. The OCT source beam 144 then enters the second optical wedge 180 through the anterior surface 186. The OCT source beam 144 is then partially reflected by the second optical wedge posterior surface 188. The portion of the OCT source beam 144 that is reflected by the posterior surface 188 becomes the reference beam 104. The portion of the OCT source beam 144 that passes through the posterior surface 188 becomes the sample beam 102. In the embodiment illustrated, each of the first and second optical wedges 178, 180 have a wedge angle 190 of 6 degrees. A suitable material for the first and second optical wedges 178, 180 can be selected. For example, the first and second optical wedges can be made from a high refractive index glass (e.g., Schott NSF6 with a refractive index of 1.7826 at wavelength 830 nm).

The first and second wedges 178 and 180 are configured to counter-act prism dispersion and color aberration that would result if only one optical wedge was used. Passing either the sample beam 102 or the reference beam 104 through a single wedge would result in prism dispersion and color aberration due to the broad bandwidth (e.g., 810 to 850 nm) of the OCT source beam 144. The wedge angles of the first and second optical wedges 178, 180 are therefore opposing. In this way, each of the OCT source beam 144, the reference beam 104, and returning portion of the sample beam 102 experiences offsetting wedges effects because the beams pass thru both of the first and second optical wedges 178, 180. For example, the reference beam 104 experiences this cancellation of the wedge effect because the reference beam 104 reflects off the second optical wedge posterior surface 188 and then propagates through the second optical wedge 180 and then through the offsetting first optical wedge 178.

In many embodiments, the OCT source beam 144 is generally unpolarized. The returning portion of the sample beam 102, however, may have any polarization including pure s-polarized, pure p-polarized or a combination of both. The polarization of the returning portion of the sample beam 102 is an uncontrolled variable due to polarization effects imparted by the eye 43. For example, birefringence of the cornea can impart polarization to the returning portion of the sample beam 102. The polarization effects caused by the eye may be dependent on position of the sample beam 102 within the eye 43 and subject to anatomical differences. Similar to an interferometer, the OCT light source and detection device 98 generates an OCT signal based on interference between the returning portion of the sample beam 102 and the reference beam 104. To achieve signal and contrast, the reference beam 104 preferably contains both polarization states. Additionally, the polarization of the source beam 144 can vary depending on the light source used and fiber optic orientation. This can vary from source to source. The purpose of the ¼w plate in the reference path is to ensure that a proper amount of both s and p polarization with respect to the sample beam are present in order to generate signal. An extreme example is the source beam may be linearly polarized in the p-direction. This p-polarized light may be completely converted to s-polarized light due to uncontrolled anatomical effects upon return in the sample path. Meanwhile in the reference path without a ¼w plate the p-polarization is preserved. Upon combining the sample and reference paths, the crossed polarized beams would fail to produce a signal. Introduction of a ¼w plate in the reference beam can convert the p-polarized light into s-polarized reference return light and therefore produce a signal. The ¼w plate is adjustable in rotation about its Z axis (clocking). Adjustment can be made on a system to system basis to optimize return signal.

In many embodiments, the pickoff/combiner assembly 100 is configured to minimize polarization effects or differences due to beam polarization. For example, as illustrated in Table 1, the illustrated embodiment of the pickoff/combiner assembly 100 is configured to minimize the angle of incidence of the beams (OCT source beam 144, sample beam 102, and reference beam 104) at all of the optical wedge surfaces 182, 184, 186, and in particular at surface 188 so as to minimize polarization effects.

TABLE 1

Example Pickoff/Combiner Assembly Incident Angles and Surface Coatings

| Surface | Beam | Glass to Air Angle | Surface Coating |
| --- | --- | --- | --- |
| 182 | 144 | 12.80 degrees | Anti-reflection |
| 184 | 144 | 2.03 degrees | Anti-reflection |
| 186 | 144 | 1.03 degrees | Anti-reflection |
| 188 | 144, 102, 104 | 11.78 degrees | Uncoated |
| 186 | 104 | 22.84 degrees | Anti-reflection |
| 184 | 104 | 21.84 degrees | Anti-reflection |
| 182 | 104 | 10.82 degrees | Anti-reflection |

The offsetting first and second optical wedges 178, 180, the low angle of incidence of the beams 144, 102, 104 relative to the surfaces 182, 184, 186, 188, and resulting generation of the OCT signal are important aspects relative to the configuration of the pickoff/combiner assembly 100. For example, a separation 192 between the first and second optical wedges 178, 180 is preferably greater than the detection range of the OCT light source and detection device 98 for a given length of the reference path 106 so as to reduce and/or eliminate etalon effects from the OCT signal. For example, the OCT detection range can be 6.6 mm in air and the separation 192 can be larger than 6.6 mm (e.g., 8 mm or larger). The etalon effect can be further mitigated by tilting the first and second wedges 178, 180 relative to each other. For example, in the illustrated embodiment, an angle 194 of the second optical wedge anterior surface 194 is 89 degrees relative to a normal to the first optical wedge posterior surface 184 so that the surfaces 184, 186 are tilted by one degree relative to each other. Although the illustrated embodiment uses a tilt angle of one degree between the surfaces 184, 186, any suitable tilt angle can be used.

Because of the low angle of the reference beam 104 relative to the OCT source beam 144, a certain amount of distance is required before the reference beam 104 is sufficiently separated from the OCT source beam 144 to accommodate the mirror 146. For example, a distance 196 (e.g., 43 mm) parallel to the OCT source beam 144 and a distance 198 (e.g., 22 mm) perpendicular to the OCT source beam 144 can be used to provide adequate room for the mirror 146.

Because the length of the reference path 106 is adjusted to match the sample path length, distances 200, 202 must be accounted for in configuring the reference path 106. The separation of the first and second optical wedges 178, 180 along with associated wedge and tilt angles cause an offset 204 between the OCT source beam 144 and the sample beam 102. The offset 204 must also be accounted for with respect to positioning optical elements between the pickoff/detection assembly 100 and the beam combiner 114.

The second optical wedge posterior surface 188 is the beam combining surface of the pickoff/detection assembly 100. The surface 188 is uncoated so as to assure reliable reflectivity by eliminating any possible coating degradation related reflectivity changes. The angle of incidence at the surface 188 is small to reduce the difference in reflectivity for s and p polarizations. It is important to control the amount of light split between the reference and sample paths. To achieve good signal (as in an interferometer) there is preferably balance in the intensity of the light from both paths. The returning portion of the sample beam 102 is the amount of return generated by reflections and scatter off of a target (e.g., a structure in the eye 43). Generally the returning portion of the sample beam 102 is relatively low and variable. In contrast, there is little light loss in the reference path 106. Therefore, to maximize light delivered into the eye 43 and to balance the returning light from both the sample and reference paths, the pickoff/combiner assembly 100 transmits more light than it reflects. Additionally, there is a further safety requirement to limit the amount of light entering the eye 43. Accordingly, as an example, for an OCT source beam 144 having about 6 mW of light and the above considerations, an 8% reflectivity can be selected as a suitable reflectivity level. The 8% reflectivity results in a pickoff percentage of 8% for the reference beam 104 and 92% for the sample beam 102 or a ratio of 11.5 to 1 sample to reference. A ratio around 10 to 1 may also be suitable. The reflectivity for the two polarizations match with respect to each other to within approximately 10%, [(8.3−7.53)/8.3=9.2%].

Each of the other surfaces 182, 184, 186 has an anti-reflection or AR coating. The low angle of incidence on these surfaces also assures polarization insensitivity. Because of the high refractive index of the glass used in the illustrated embodiment, a simple protected magnesium fluoride $MgF_2$ coating can be used resulting in a low reflectivity of <0.5% per surface. The simple $MgF_2$ coating has the advantages of consistent control in fabrication and low probability of coating degradation.

Using high refractive index glass for the first and second optical wedges 178, 180 provides advantages over low refractive index glass such as: high reflectivity (Fresnel reflection) for the uncoated surface at low angle of incidence, a higher refractive angle for the same angle of incidence thereby providing separation of the beams, and a simple $MgF_2$ coating provides excellent anti-reflection i.e. lower reflectivity. A disadvantage of using high refractive index glass for the first and second optical wedges 178, 180 is the higher dispersion usually associated with the higher refractive index. The higher dispersion, however, is offset by the offsetting wedge geometry.

Variations in the configuration of the pickoff/detection assembly 100 are possible. For example, the pickoff/detection assembly 100 might be configured as a single element depending on the bandwidth/wavelengths of the OCT source beam 144 and other relevant mechanical considerations. The single element may be a plate beam splitter, a wedged plate, a cube, or other known beam splitting element. The wedge angle 190 of the second optical wedge 180 can be different from the wedge angle 190 of the first optical wedge 178. The second optical wedge 180 can also be made from a different glass from the first optical wedge 178. Beam dumps and baffles (not illustrated) can also be used for unused light reflected from the surfaces 182, 184, 186, 188.

Referring back to FIGS. 4A, 4B, and 4C, after exiting the pickoff/detection assembly 100, the sample beam 102 is reflected by mirrors 206, 208 and then passes through an aperture 210 before being incident on the beam combiner 114. The sample beam 102 is transmitted through the beam combiner 112 and is then reflected by a mirror 212 so as to be incident on the beam combiner 82. The sample beam 102 is transmitted through the beam combiner 82 into the shared optics 50. Beam aperture 210 may be used to limit the amount of light delivered to the eye. This limit may be set by optical hazard considerations and limits, for example, as set by international standards. The beam aperture 154 in the reference arm 106 may be used to fine tune the balance of light in the combined reference and sample arms. The beam aperture 154 can also used to limit the amount of light directed into the OCT detector 98 to prevent detector saturation, for example. The aperture 154 may also be used to match reference beam size and numerical aperture to that of the sample.

The mirrors 146, 150, 156, 158, 164, 166, 168, 174, 176, 206, 208 in the ranging subsystem 46 can be metal (e.g., silver) coated if possible to reduce and prevent adverse dispersion effects. Alternatively, transmission within the ranging subsystem 46 can be through complex dielectrics where suitable as opposed to reflecting to reduce and prevent adverse dispersion effects.

The alignment guidance subsystem 48 includes the aim beam light source 110 and the aim path 112. The aim path 112 transmits the aim beam 108 emitted by the aim beam light source 110 to the beam combiner 114. After being emitted by the aim beam light source 110, the aim beam 108 is reflected by mirrors 214, 216 and then passes through a coupling lens 218 into an optical fiber 220. The aim beam 108 emerges from the optical fiber 220 so as to pass through a collimating lens 222, then through an aperture 224, and then through a beam expander 226. The beam expander 226 propagates the aim beam 108 over a distance while accommodating positional and/or directional variability of the aim beam 108, thereby providing increased tolerance for component variation. The beam expander 226 relays an image of the aperture 224 to a plane near the galvo mirrors 86 and 88. This plane is an alignment reference plane for the system. After the beam expander 226, the aim beam 108 is reflected by mirrors 228, 230, 232 so as to be incident on the beam combiner 114, which reflects the aim beam 108 toward the mirror 212. The aim beam 108 is reflected by the mirror 212 so at to be incident on the beam combiner 82. The aim beam 108 passes through the beam combiner 82 and continues into the shared optics 50.

In many embodiments, the aim beam 108 can be used as a system alignment aid. By checking/ensuring suitable system alignment on a suitable reoccurring time frame, patient safety may be enhanced. The aim beam 108 can also be used as a targeting aid for directing the laser pulse beam 66 at target locations in the eye 43. The aim beam 108 can also be used as a fixation light source to give the patient something to look at to control orientation of the eye 43. The aim beam 108 can also be used for monitoring the angle and position of the X, Y, & Z actuators. This could be accomplished by placing a detector or detectors such as position sensing detectors in the beam or a pickoff of the beam. A pickoff location may be the reflections off of beam combiner 90. In many embodiments, the aim beam light source 110 includes a diode laser that is directly controlled via electrical input with no attenuation required.

The shared optics 50 provides a common optical path for the laser pulse beam 66, the sample beam 102, and the aim beam 108. The shared optics 50 includes the beam combiner 114, the beam combiner 82, the Z-telescope 84, the X-scan device 86, the Y-scan device 88, the beam combiner 90, and the objective lens assembly 94. The shared optics 50 also includes periscopes 234, 236, which provide an adjustable means to align the laser pulse beam 66, the sample beam 102, and the aim beam 108 with the downstream optical path through the downstream portion of the shared optics 50, the patient interface 52, and into the eye 43.

In many embodiments, the shared optics 50 is configured to distribute aberration correction balance amongst the Z-telescope 84, the objective lens assembly 94, and the patient interface lens 96. Specifically, in many embodiments, the Z-telescope 84, the objective lens assembly 94, and the patient interface lens 96 are configured such that the total aberration contribution of all the optical elements in the Z-telescope 84, the objective lens assembly 94, and the patient interface lens 96 sums to zero as nearly as practicable.

The alignment guidance subsystem 48 further includes the video subsystem 92. The video subsystem 92 includes the camera 116, the illumination light source 118, and the beam combiner 120.

The video subsystem 92 can be designed for one or more modes of operation. For example, the video subsystem 92 can be designed to provide approach guidance during docking of the eye 43 to the laser eye surgery system 2. The docking approach guidance mode of operation can utilize dark-field cross-polarized illumination. The docking approach guidance mode of operation can utilize bright field fixation. Once the eye 43 is docked to the laser eye surgery system 2, the video subsystem 92 can provide a dark-field cross polarization image of the incised region of the eye 43 and the patient interface 52. Once the eye is docked to the laser eye surgery system 2, the video subsystem 92 can provide bright-field illumination for automated iris detection.

Figure 7:
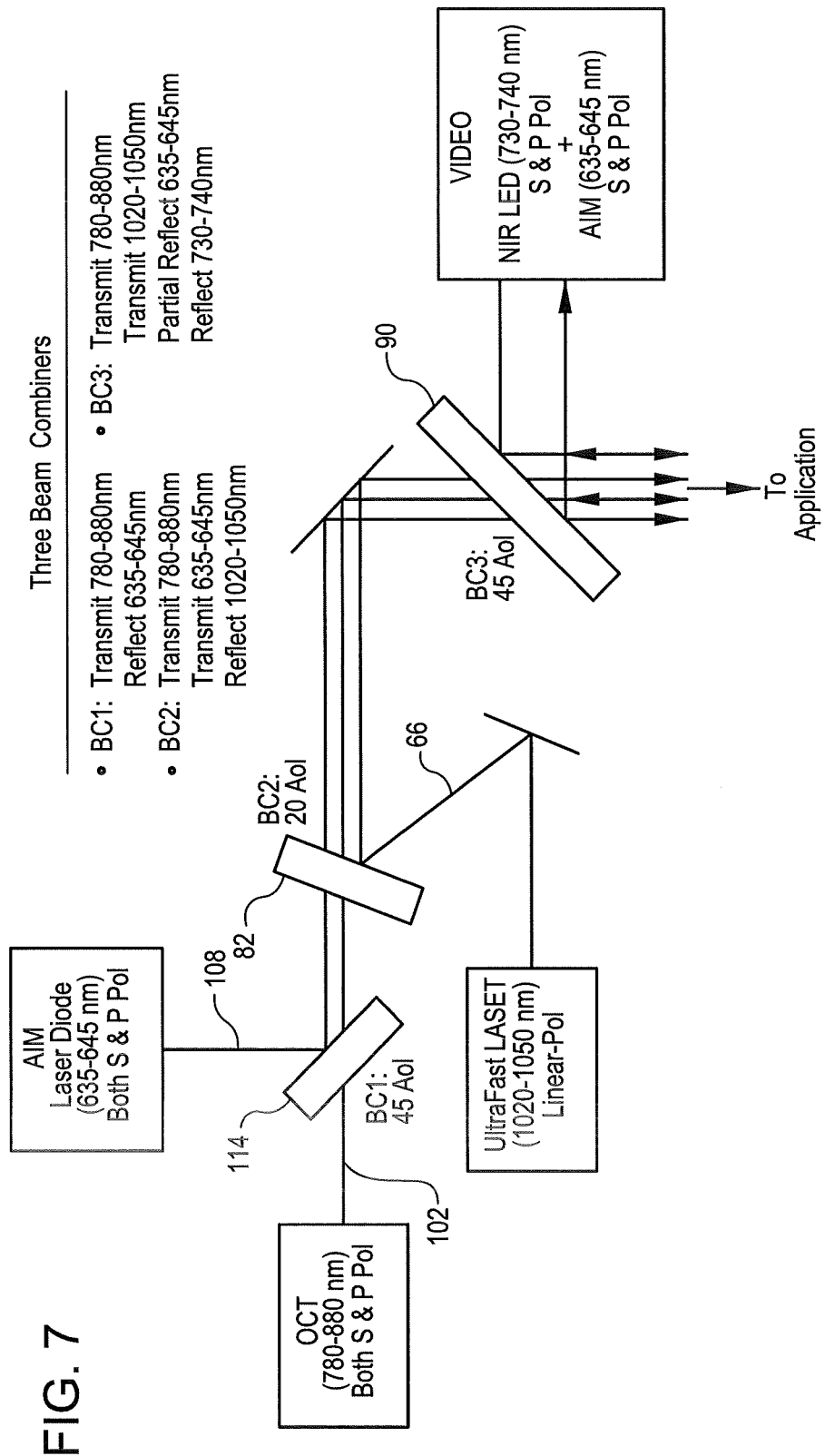
FIG. 7 is a simplified diagram illustrating aspects of beam combiners of a laser eye surgery system, in accordance with many embodiments.

FIG. 7 illustrates transmission and reflectivity characteristics of the beam combiner 114 used to combine the aim beam 108 and the OCT sample beam 102, the beam combiner 82 used to combine the laser pulse beam 66 with both the aim beam 108 and the OCT sample beam 102, and the beam combiner 90 used to reflect an image to the video subsystem 92. The beam combiner 114 is configured to transmit the OCT sample beam 102 and reflect the aim beam 108. For example, the beam combiner 114 can be configured to transmit wavelengths from 780 to 880 nm (both s and p polarizations) and reflect wavelengths from 635 to 645 nm. The beam combiner 82 is configured to reflect the laser pulse beam 66 while transmitting both the OCT sample beam 102 and the aim beam 108. For example, the beam combiner 82 can be configured to reflect wavelengths from 1020 to 1050 nm (including linear polarization) and transmit wavelengths from both 780 to 880 nm and 635 to 645 nm. The beam combiner 90 is configured to transmit each of the OCT sample beam 102 and the laser pulse beam 66, partially reflect the aim beam 108, and reflect illumination light from the illumination light source (e.g., near infrared LED illumination-wavelengths from 730 to 740 nm).

Figure 8:
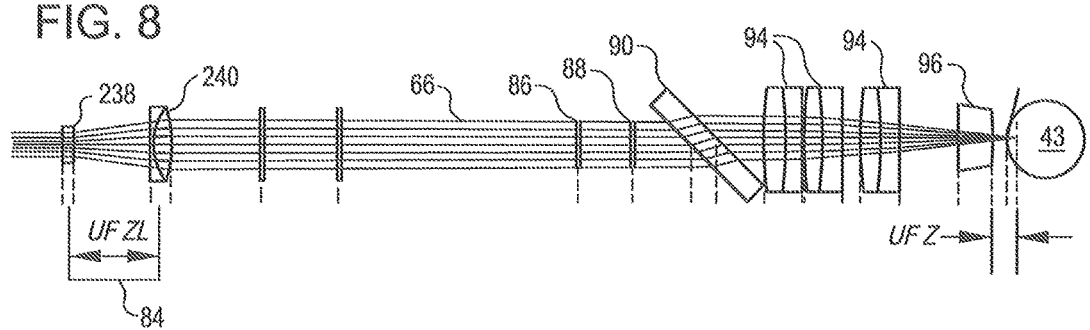
FIG. 8 is a simplified diagram illustrating aspects of using a Z-telescope to change a depth of focus of a treatment beam within an eye, in accordance with many embodiments.

FIG. 8 illustrates the use of the Z-telescope 84 to focus the laser pulse beam 66 to different depths within the eye 43. In the illustrated embodiment, the Z-telescope 84 includes a lens 238 and a lens 240. The distance (UF ZL) between the lenses 238, 240 determines the depth in the eye 43 at which the laser pulse beam 66 is focused. The distance (UF ZL) determines whether the laser pulse beam 66 is diverging (becoming wider) as the laser pulse beam 66 travels between the lens 240 and the X-scan device 86, is converging (becoming narrower) as the laser pulse beam 66 travels between the lens 240 and the X-scan device 86, or is neither diverging or converging (constant width) as the laser pulse beam 66 travels between the lens 240 and the X-scan device 86. The more the laser pulse beam 66 is diverging between the lens 240 and the X-scan device 86, the deeper the depth in the eye 43 at which the laser pulse beam 66 is focused. The more the laser pulse beam 66 is converging between the lens 240 and the X-scan device 86, the shallower the depth in the eye 43 at which the laser pulse beam 66 is focused. Table 2 provides example values for the distance (UF ZL) between the lenses 238, 240, as well as corresponding values of the depth of the focal point (UF Z), corresponding values of the resulting numerical aperture (NA), corresponding values of the diameter of the laser pulse beam 66 at the lens 240, and corresponding values of the diameter of the laser pulse beam 66 at the X-scan device 86.

TABLE 2

Example Z-telescope settings and corresponding values of focus depth, numerical aperture, and beam diameters for the laser pulse treatment beam.

| UF ZL (mm) | UF Z (mm) | NA | Beam Diameter at Lens 240 (mm) | Beam Diameter at X-scan Device 86 (mm) |
|---|---|---|---|---|
| 29.314 | 5.000 | 0.128 | 18.61 | 15.34 |
| 27.399 | 8.000 | 0.137 | 18.08 | 16.14 |
| 24.950 | 11.283 | 0.149 | 17.40 | 17.16 |
| 24.600 | 11.709 | 0.150 | 17.30 | 17.30 |
| 20.564 | 16.000 | 0.169 | 16.18 | 18.99 |

Figure 9:
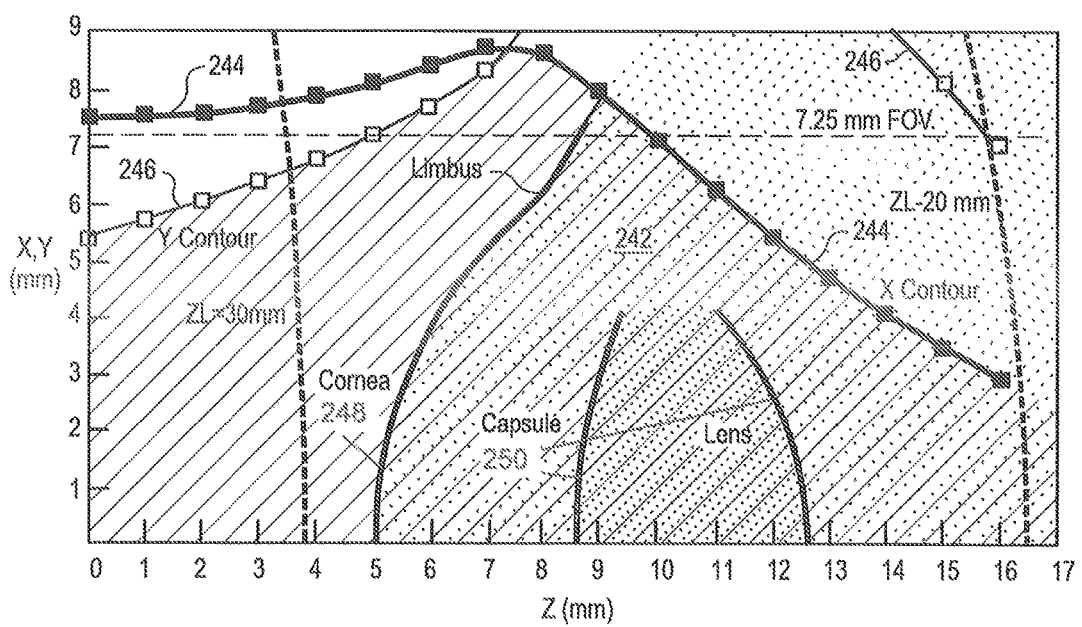
FIG. 9 diagrammatically illustrates a volume within an eye in which incisions can be formed by a laser eye surgery system, in accordance with many embodiments.

In many embodiments, the laser eye surgery system 2 is configured to be capable of delivering laser pulses to tightly focused points to disrupt and thereby incise tissue throughout a desired treatment volume within the eye 43. For example, FIG. 9 is a diagram illustrating a predicted treatment volume 242 (hatched area) within which the laser eye surgery system 2 is capable of incising tissue. The predicted treatment volume 242 is bounded in the transverse directions by an x-direction boundary 244 and a y-direction boundary 246. Boundary conditions are determined by optical model simulation of threshold levels taking into account numerical aperture, aberration control, beam quality of the laser, polarization of the laser, pulse width, and optical train transmission anchored to empirically determined levels of tissue breakdown. To ensure that there is cutting, the boundaries factor in a margin above this threshold. A 2 times or 4 times margin above an empirically determined threshold is reasonable given the range of variation that goes into determining threshold levels. The predicted treatment volume 242 is wider in the x direction for z values (axial distance from the posterior surface of the patient interface lens 96) of less than about 7.25 mm and is wider in the y direction for z values of greater than about 7.25 mm. As shown, the predicted treatment volume 242 encompasses the cornea 248 and lens capsule 250 of the eye 43, thereby enabling the creation of incisions at any desired location in the cornea 248 and lens capsule 250.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A ranging system configured to produce a source beam used to locate one or more structures of an eye, the ranging system including an optical coherence tomography (OCT) pickoff assembly for dividing an OCT light source beam into a sample beam and a reference beam, the OCT pickoff assembly comprising:
   a first optical wedge; and
   a second optical wedge separated from the first optical wedge,
   wherein:
   the source beam propagates through the first optical wedge and into the second optical wedge;
   each of the first and second optical wedges having non-parallel anterior and posterior surfaces with respect to entry and exit of the source beam as the source beam propagates through the first optical wedge and into the second optical wedge;
   the second optical wedge posterior surface is partially reflective so as to divide the source beam into the sample beam and the reference beam;
   the first and second optical wedges have a same wedge angle as each other and are arranged such that the wedge angles are opposing;
   the sample beam propagates out of the second optical wedge through the posterior surface of the second optical wedge;
   the reference beam propagates out of the second optical wedge through the anterior surface of the second optical wedge and propagates back through the first optical wedge and along a reference optical path;
   the first and second optical wedges are separated by a distance greater than a detection range of the ranging system to inhibit etalon effects; and
   angles of incidence at all surfaces of the first and second optical wedges are disposed such that the OCT pickoff assembly is substantially polarization insensitive.

2. The system of claim 1, wherein a wedge angle of the first and second optical wedges is each in a range from 3 degrees to 10 degrees.

3. The system of claim 2, wherein the wedge angle of the first and second optical wedges is each in a range from 5 degrees to 7 degrees.

4. The system of claim 1, wherein the first and second optical wedges are made from the same material having a refractive index of greater than 1.50 with respect to the source beam.

5. The system of claim 4, wherein the refractive index is greater than 1.70 with respect to the source beam.

6. The system of claim 1, wherein:
   the first optical wedge anterior and posterior surfaces have an anti-reflection coating;
   the second optical wedge anterior surface has the anti-reflection coating; and
   the second optical wedge posterior surface is uncoated.

7. The system of claim 6, wherein the anti-reflection coating is magnesium fluoride ($MgF_2$).

8. The system of claim 1, wherein the source beam has an angle of incidence on the second optical wedge posterior surface of less than 25 degrees.

9. The system of claim 8, wherein the angle of incidence is less than 15 degrees.

10. The system of claim 1, wherein the second optical wedge anterior surface and the first optical wedge posterior surface deviate from parallel by 0.25 degrees to 3.0 degrees.

11. An optical coherence tomography (OCT) pickoff assembly for dividing an OCT light source beam into a sample beam and a reference beam, comprising:
a first optical wedge; and
a second optical wedge separated from the first optical wedge,
wherein:
the source beam propagates through the first optical wedge and into the second optical wedge;
each of the first and second optical wedges having non-parallel anterior and posterior surfaces with respect to entry and exit of the source beam as the source beam propagates through the first optical wedge and into the second optical wedge;
the second optical wedge posterior surface is partially reflective so as to divide the source beam into the sample beam and the reference beam;
the first and second optical wedges have a same wedge angle as each other and are arranged such that the wedge angles are opposing;
the sample beam propagates out of the second optical wedge through the posterior surface of the second optical wedge;
the reference beam propagates out of the second optical wedge through the anterior surface of the second optical wedge and propagates back through the first optical wedge and along a reference optical path;
the second optical wedge posterior surface is uncoated; and
the second optical wedge anterior surface and the first optical wedge posterior surface are non-parallel, so as to inhibit etalon effects.

12. The assembly of claim 11, wherein a wedge angle of the first and second optical wedges is each in a range from 3 degrees to 10 degrees.

13. The assembly of claim 12, wherein the wedge angle of the first and second optical wedges is each in a range from 5 degrees to 7 degrees.

14. The system of claim 13, wherein the second optical wedge anterior surface and the first optical wedge posterior surface deviate from parallel by 0.50 degrees to 1.5 degrees.

15. The assembly of claim 11, wherein the first and second optical wedges are made from the same material having a refractive index of greater than 1.50 with respect to the source beam.

16. The assembly of claim 15, wherein the refractive index is greater than 1.70 with respect to the source beam.

17. The assembly of claim 11, wherein:
the first optical wedge anterior and posterior surfaces have an anti-reflection coating;
the second optical wedge anterior surface has the anti-reflection coating; and
the second optical wedge posterior surface is uncoated.

18. The assembly of claim 17, wherein the anti-reflection coating is magnesium fluoride ($MgF_2$).

19. The assembly of claim 11, wherein the source beam has an angle of incidence on the second optical wedge posterior surface of less than 25 degrees.

20. The assembly of claim 19, wherein the angle of incidence is less than 15 degrees.

21. The assembly of claim 11, wherein the second optical wedge anterior surface and the first optical wedge posterior surface deviate from parallel by 0.25 degrees to 3.0 degrees.

22. The assembly of claim 11, wherein the second optical wedge anterior surface and the first optical wedge posterior surface deviate from parallel by 0.50 degrees to 1.5 degrees.

* * * * *